US007485333B2

(12) United States Patent
Pacetti et al.

(10) Patent No.: US 7,485,333 B2
(45) Date of Patent: Feb. 3, 2009

(54) METHOD OF USING A STENT MOUNTING DEVICE TO COAT A STENT

(75) Inventors: Stephen D. Pacetti, San Jose, CA (US); Plaridel K. Villareal, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 785 days.

(21) Appl. No.: 10/660,853

(22) Filed: Sep. 12, 2003

(65) Prior Publication Data

US 2005/0261764 A1 Nov. 24, 2005

Related U.S. Application Data

(62) Division of application No. 09/896,000, filed on Jun. 28, 2001, now Pat. No. 6,673,154.

(51) Int. Cl.
*B05C 13/00* (2006.01)
*A61L 33/00* (2006.01)
*B05D 3/12* (2006.01)
*B05D 1/02* (2006.01)

(52) U.S. Cl. .................... 427/2.24; 427/2.11; 427/2.25; 427/421.1; 427/346; 118/500; 118/501; 118/503

(58) Field of Classification Search ................. 118/423, 118/500, 501, 502, 503; 427/2.1, 2.24, 230, 427/232, 233, 235

See application file for complete search history.

(56) References Cited

U.S. PATENT DOCUMENTS

| | | | | |
|---|---|---|---|---|
| 2,845,346 A * | 7/1958 | Scanlan et al. | 419/2 |
| 4,629,563 A | 12/1986 | Wrasidlo | 210/500.34 |
| 4,733,665 A | 3/1988 | Palmaz | 128/343 |
| 4,800,882 A | 1/1989 | Gianturco | 128/343 |
| 4,886,062 A | 12/1989 | Wiktor | 128/343 |
| 4,906,423 A | 3/1990 | Frisch | 264/48 |
| 5,037,427 A | 8/1991 | Harada et al. | 606/108 |
| 5,171,445 A | 12/1992 | Zepf | 210/500.27 |
| 5,188,734 A | 2/1993 | Zepf | 210/490 |
| 5,229,045 A | 7/1993 | Soldani | 264/41 |
| 5,229,211 A * | 7/1993 | Murayama et al. | 428/424.4 |
| 5,234,457 A | 8/1993 | Andersen | 606/198 |
| 5,308,338 A * | 5/1994 | Helfrich | 604/175 |
| 5,537,729 A | 7/1996 | Kolobow | 29/527.2 |
| 5,611,775 A | 3/1997 | Machold et al. | 604/53 |
| 5,624,411 A | 4/1997 | Tuch | 604/265 |
| 5,628,786 A | 5/1997 | Banas et al. | 623/1 |
| 5,772,864 A | 6/1998 | Møller et al. | 205/73 |
| 5,788,626 A | 8/1998 | Thompson | 600/36 |
| 5,820,917 A | 10/1998 | Tuch | 427/2.1 |
| 5,823,996 A | 10/1998 | Sparks | 604/96 |
| 5,833,659 A | 11/1998 | Kranys | 604/96 |

(Continued)

OTHER PUBLICATIONS

Pacetti et al., A Mandrel for Supporting a Stent and a Method of Using the Mandrel to Coat a Stent, filed Jun. 27, 2001, U.S. Appl. No. 09/894,248.

*Primary Examiner*—William Phillip Fletcher, III
*Assistant Examiner*—Cachet I Sellman
(74) *Attorney, Agent, or Firm*—Squire, Sanders & Dempsey, L.L.P.

(57) ABSTRACT

A method of coating a stent using a mounting device is provided.

65 Claims, 3 Drawing Sheets

U.S. PATENT DOCUMENTS 5,855,598 A 1/1999 Pinchuk ......................... 623/1
5,865,814 A 2/1999 Tuch .......................... 604/265
5,895,407 A 4/1999 Jayaraman .................. 606/198
5,897,911 A 4/1999 Loeffler ..................... 427/2.25
5,922,393 A 7/1999 Jayaraman .................. 427/2.3
5,935,135 A 8/1999 Bramfitt et al. ............. 606/108
5,948,018 A 9/1999 Dereume et al. ............... 623/1
6,010,573 A 1/2000 Bowlin ....................... 118/620
6,045,899 A 4/2000 Wang et al. .............. 428/315.7
6,056,993 A 5/2000 Leidner et al. ............. 427/2.25
6,120,847 A 9/2000 Yang et al. .................. 427/335
6,126,686 A 10/2000 Badylak et al. ............ 623/1.24
6,153,252 A * 11/2000 Hossainy et al. ............. 427/2.3
6,156,373 A 12/2000 Zhong et al. ............... 427/2.28
6,214,115 B1 4/2001 Taylor et al. ................ 118/423
6,245,099 B1 6/2001 Edwin et al. ............... 623/1.13
6,258,121 B1 7/2001 Yang et al. ................. 623/1.46
6,279,368 B1 8/2001 Escano et al. .............. 72/342.1
6,322,847 B1 11/2001 Zhong et al. ............... 427/2.28
6,346,856 B1 * 2/2002 Myers et al. ................ 330/252
6,364,903 B2 4/2002 Tseng et al. ............... 623/1.15
6,387,118 B1 5/2002 Hanson ..................... 623/1.11
6,395,326 B1 * 5/2002 Castro et al. ............... 427/2.24
6,521,284 B1 * 2/2003 Parsons et al. ............. 427/2.24
6,527,863 B1 3/2003 Pacetti et al. ................ 118/500
6,565,659 B1 5/2003 Pacetti et al. ................ 118/500
6,572,644 B1 6/2003 Moein ....................... 623/1.11
6,605,154 B1 * 8/2003 Villareal ..................... 118/500
2003/0104129 A1 * 6/2003 Mino et al. ................. 427/346
2003/0215564 A1 * 11/2003 Heller et al. ............... 427/2.25

* cited by examiner

METHOD OF USING A STENT MOUNTING DEVICE TO COAT A STENT

CROSS REFERENCE

This is a divisional application of U.S. Ser. No. 09/896,000, which was filed on Jun. 28, 2001 now U.S. Pat. No. 6,673, 154.

BACKGROUND OF THE INVENTION

1. Field of the Invention

This invention relates to a stent mounting device and a method of coating a stent using the device.

2. Description of the Background

Blood vessel occlusions are commonly treated by mechanically enhancing blood flow in the affected vessels, such as by employing a stent. Stents act as scaffoldings, functioning to physically hold open and, if desired, to expand the wall of the passageway. Typically stents are capable of being compressed, so that they can be inserted through small lumens via catheters, and then expanded to a larger diameter once they are at the desired location. Examples in the patent literature disclosing stents include U.S. Pat. No. 4,733,665 issued to Palmaz, U.S. Pat. No. 4,800,882 issued to Giant-urco, and U.S. Pat. No. 4,886,062 issued to Wiktor.

FIG. 1 illustrates a conventional stent 10 formed from a plurality of struts 12. The plurality of struts 12 are radially expandable and interconnected by connecting elements 14 that are disposed between adjacent struts 12, leaving lateral openings or gaps 16 between adjacent struts 12. Struts 12 and connecting elements 14 define a tubular stent body having an outer, tissue-contacting surface and an inner surface.

Stents are used not only for mechanical intervention but also as vehicles for providing biological therapy. Biological therapy can be achieved by medicating the stents. Medicated stents provide for the local administration of a therapeutic substance at the diseased site. Local delivery of a therapeutic substance is a preferred method of treatment because the substance is concentrated at a specific site and thus smaller total levels of medication can be administered in comparison to systemic dosages that often produce adverse or even toxic side effects for the patient.

One method of medicating a stent involves the use of a polymeric carrier coated onto the surface of the stent. A composition including a solvent, a polymer dissolved in the solvent, and a therapeutic substance dispersed in the blend is applied to the stent by immersing the stent in the composition or by spraying the composition onto the stent. The solvent is allowed to evaporate, leaving on the stent strut surfaces a coating of the polymer and the therapeutic substance impregnated in the polymer.

A shortcoming of the above-described method of medicating a stent is the potential for coating defects. While some coating defects can be minimized by adjusting the coating parameters, other defects occur due to the nature of the interface between the stent and the apparatus on which the stent is supported during the coating process. A high degree of surface contact between the stent and the supporting apparatus can provide regions in which the liquid composition can flow, wick, and collect as the composition is applied. As the solvent evaporates, the excess composition hardens to form excess coating at and around the contact points between the stent and the supporting apparatus. Upon the removal of the coated stent from the supporting apparatus, the excess coating may stick to the apparatus, thereby removing some of the coating from the stent and leaving bare areas. Alternatively, the excess coating may stick to the stent, thereby leaving excess coating as clumps or pools on the struts or webbing between the struts.

Thus, it is desirable to minimize the potential for coating defects generated by the interface between the stent and the apparatus supporting the stent during the coating process. Accordingly, the present invention provides for a device for supporting a stent during the coating application process. The invention also provides for a method of coating the stent supported by the device.

SUMMARY OF THE INVENTION

The present invention provides an apparatus for supporting a stent during a process of coating the stent The apparatus includes a member for supporting a stent during the coating process, wherein a section of the member includes a porous surface capable of receiving the coating substance during the coating process. The pores can have a diameter between about 0.2 microns and about 50 microns.

In one embodiment, the member includes a first member for making contact with a first end of the stent and a second member for making contact with a second end of the stent. In such an embodiment, the pores can be located on at least a region of the surface of the first or second members. The first or second member can be made from a metallic material such as 300 Series stainless steel, 400 Series stainless steel, titanium, tantalum, niobium, zirconium, hafnium, and cobalt chromium alloys. The first or second member can also be made from a polymeric material such as, but not limited to, regenerated cellulose, cellulose acetate, polyacetal, polyetheretherketone, polyesters, highly hydrolyzed polyvinyl alcohol, nylon, polyphenylenesulfide, polyethylene, polyethylene terephthalate, polypropylene, and combinations thereof. The first or second member can also be made from ceramics such as, but not limited to, zirconia, silica, glass, sintered calcium phosphates, calcium sulfate, and titanium dioxide. In another embodiment, a layer can be disposed on the surface of the first or second member to absorb coating material that comes into contact with the layer.

In one embodiment, the first and second members have inwardly tapered ends that penetrate at least partially in the first and second ends of the stent and are in contact with the first and second ends of the stent. In another embodiment, the apparatus additionally includes a third member for extending within the stent and for securing the first member to the second member.

In an aspect of the present invention, a method of coating a stent is disclosed including positioning a stent on a mounting assembly, wherein a section of the mounting assembly includes a plurality of pores; and applying a coating composition to a surface of the stent. wherein the pores are configured to receive at least some of the coating composition applied to the surface of the stent that overflows from the surface during the application of the coating composition. In an embodiment, the act of applying a coating composition includes spraying the composition onto the stent.

In one embodiment, the method also includes at least partially expanding the stent prior to applying the coating composition. The method can include rotating the stent about the longitudinal axis of the stent as the coating composition is applied to the stent. The method can also include moving the stent in a linear direction along the longitudinal axis of the stent as the coating composition is applied to the stent.

Also provided is a support assembly for a stent. The support assembly includes a member for supporting a stent, wherein the member includes an absorbing layer for at least partially absorbing some of the coating material that comes into contact with the absorbing layer.

DETAILED DESCRIPTION

Embodiments of the Mounting Assembly

Figure 1:
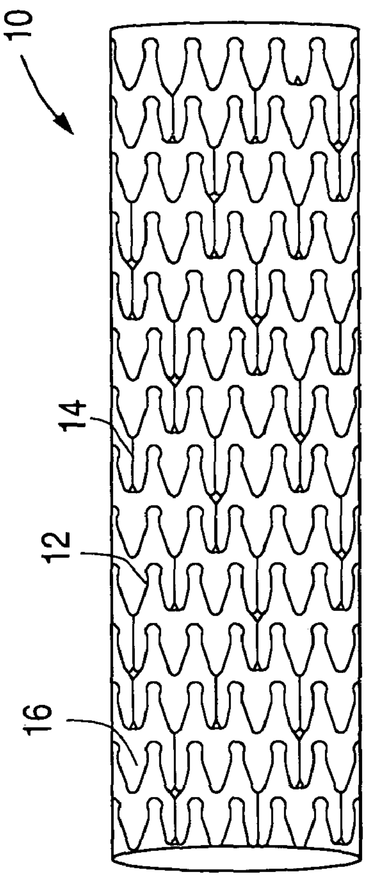
FIGURE 1 (PRIOR ART)
FIG. 1 illustrates a conventional stent.
Figure 2A:
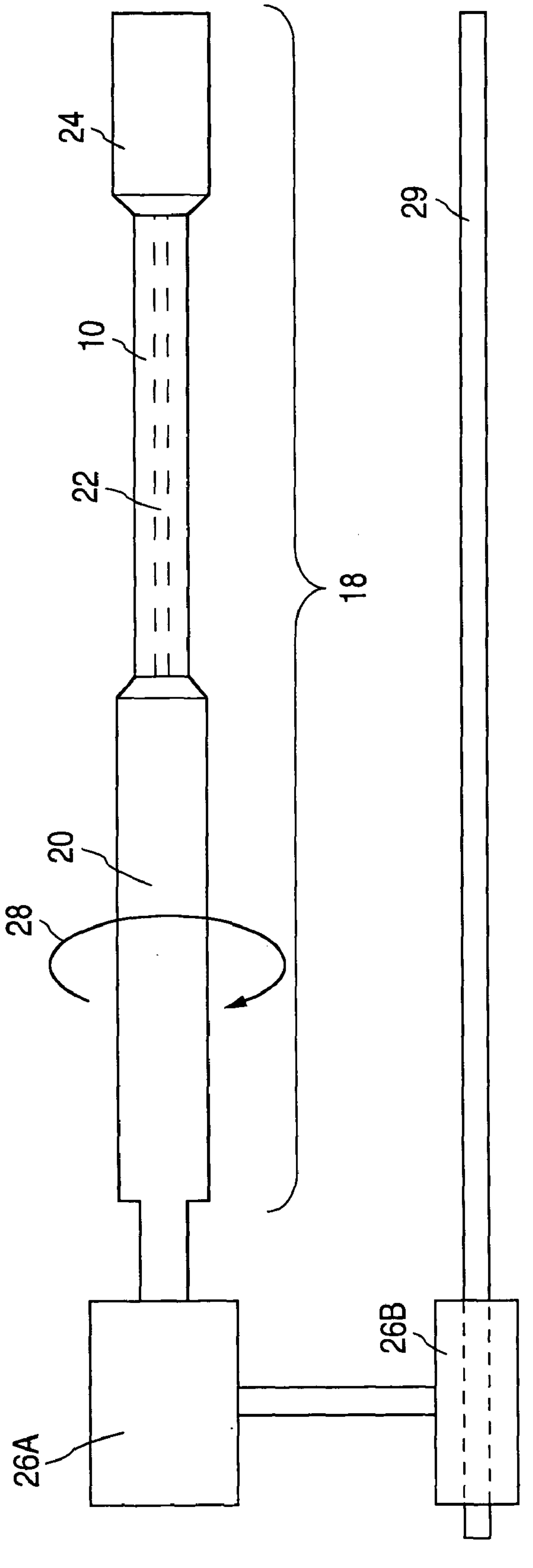
FIG. 2A illustrates a mounting assembly for supporting a stent in accordance with one embodiment of the present invention.

Referring to FIG. 2A, a mounting assembly 18 for supporting stent 10 is illustrated to include a support member 20, a mandrel 22, and a lock member 24. Support member 20 can connect to a motor 26A so as to provide rotational motion about the longitudinal axis of stent 10, as depicted by arrow 28, during the coating process. Another motor 26B can also be provided for moving support member 20 in a linear direction, back and forth, along a rail 29. The type of stent 10 is not of critical importance and can include radially expandable stents and stent-grafts.

Figure 2B:
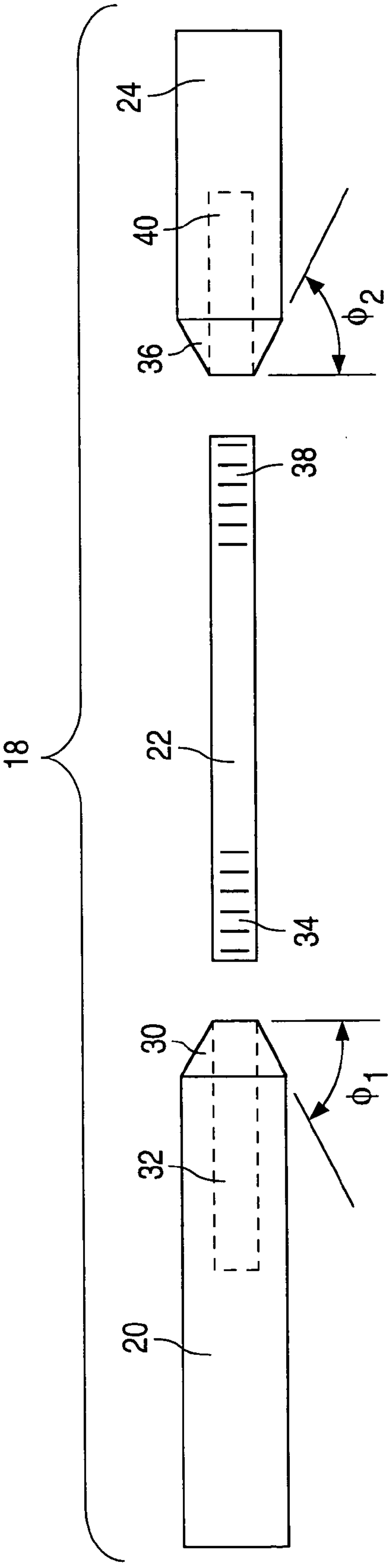
FIG. 2B illustrates an expanded view of the mounting assembly in accordance with one embodiment of the present invention.

Referring to FIG. 2B, support member 20 includes a coning end portion 30, tapering inwardly at an angle $\phi_1$ of about 15° to about 75°, more narrowly from about 30° to about 60°. By way of example, angle $\phi_1$ can be about 45°. In accordance with one embodiment, mandrel 22 can be permanently affixed to coning end portion 30. Alternatively, support member 20 can include a bore 32 for receiving a first end 34 of mandrel 22. First end 34 of mandrel 22 can be threaded to screw into bore 32. Alternatively, a non-threaded first end 34 and bore 32 combination can be employed such that first end 34 can be press-fitted or friction-fitted within bore 32 to prevent movement of stent 10 on mounting assembly 18. Bore 32 should be deep enough so as to allow mandrel 22 to securely mate with support member 20. The depth of bore 32 can also be over-extended so as to allow a significant length of mandrel 22 to penetrate bore 32. This would allow the length of mandrel 22 to be adjusted to accommodate stents of various sizes. In commercial embodiments, support member 20 can be disposable or capable of being cleaned after each use, for example in a solvent or oxidizing bath, or by pyrolizing out any absorbed coating materials via heating at high temperatures.

The outer diameter of mandrel 22 should be smaller than the inner diameter of stent 10 so as to prevent the outer surface of mandrel 22 from making contact with the inner surface of stent 10. A sufficient clearance between the outer surface of mandrel 22 and the inner surface of stent 10 should be provided to prevent mandrel 22 from obstructing the pattern of the stent body during the coating process. By way of example, the outer diameter of mandrel 22 can be from about 0.010 inches (0.254 mm) to about 0.017 inches (0.432 mm) when stent 10 has an inner diameter of between about 0.025 inches (0.635 mm) and about 0.035 inches (0.889 mm).

Lock member 24 includes a coning end portion 36 having an inwardly tapered angle $\phi_2$. Angle $\phi_2$ can be the same as or different than the above-described angle $\phi_1$. A second end 38 of mandrel 22 can be permanently affixed to lock member 24 if end 34 is disengagable from support member 20. Alternatively, in accordance with another embodiment, mandrel 22 can have a threaded second end 38 for screwing into a bore 40 of lock member 24. Bore 40 can be of any suitable depth that would allow lock member 24 to be incrementally moved closer to support member 20. Accordingly, stents 10 of any length can be securely pinched between support and lock members 20 and 24. In accordance with yet another embodiment, a non-threaded second end 38 and bore 40 combination is employed such that second end 38 can be press-fitted or friction-fitted within bore 40. In commercial embodiments, lock member 24 can be disposable or capable of being cleaned after each use.

Figure 3A:
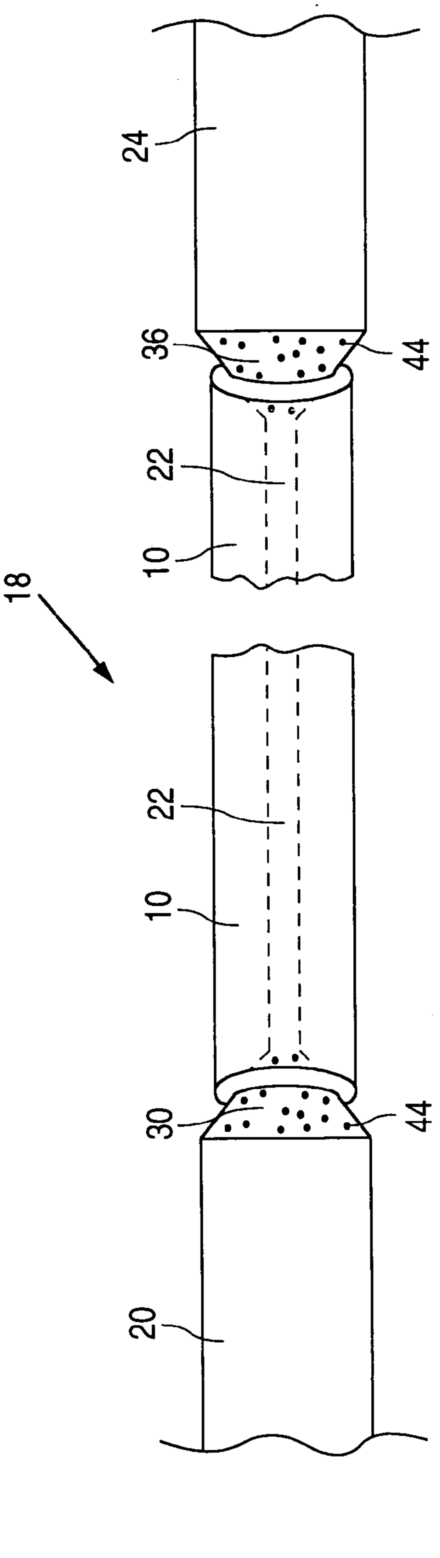
FIG. 3A illustrates the interface between the mounting assembly and the stent.
Figure 3B:
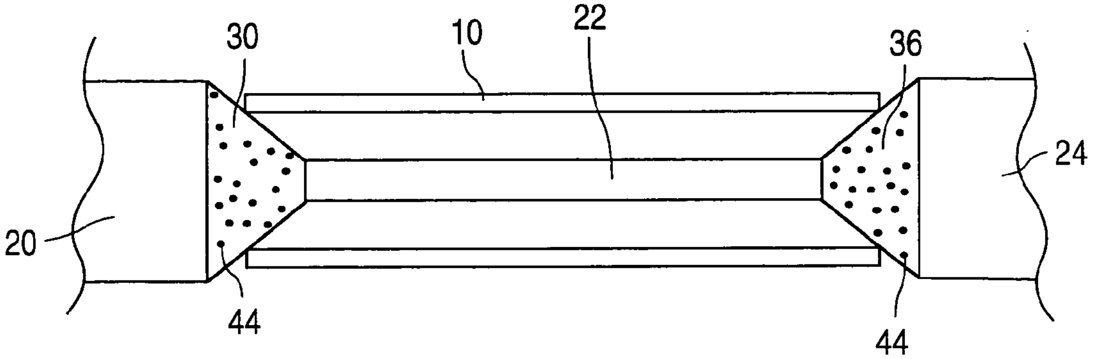
FIG. 3B is a cross-sectional view of the interface between the mounting assembly and the stent in FIG. 3A.

Mounting assembly 18 supports stent 10 via coning end portions 30 and 36. FIGS. 3A and 3B illustrate the interface between coning end portions 30 and 36 and each end of stent 10 so as to provide minimal contact between stent 10 and mounting assembly 18. Opposing forces exerted from support and lock members 20 and 24, for securely pinching stent 10, should be sufficiently strong so as to prevent any significant movement of stent 10 on mounting assembly 18. However, the exerted force should not compress stent 10 so as to distort the body of stent 10. Over or under application of support force can lead to coating defects, such as non-uniformity of the coating thickness.

In addition to supporting stent 10 with minimal contact, coning end portions 30 and 36 also function to reduce buildup of coating materials at the stent 10—mounting assembly 18 interface. Coning end portions 30 and 36 should be able to absorb the coating substance applied to stent 10. Thus, excess coating substance is absorbed into coning end portions 30 and 36 and drawn away from stent 10 during the coating process, further minimizing the potential for webbing and other coating defects at the interface between stent 10 and mounting assembly 18.

In one embodiment, the particular material selected for coning end portions 30 and 36 can be any material having a plurality of pores 44 suitable to receive or absorb the coating substance deposited thereon during the coating process. Pores 44 can be interconnected. Interconnected pore structures are also known as open pore systems as opposed to closed pore systems in which pores 44 are isolated from one another. Interconnected pores 44 provide a network for moving and holding the coating substance, thus enabling coning end portions 30 and 36 to hold a larger amount of the coating substance than coning end portions 30 and 36 having discrete pores 44, each with a fixed capacity for uptake of the substance. The diameter of pores 44 can be from about 0.2 microns to about 50 microns, for example about 1 micron.

Coning end portions 30 and 36 can be made of materials having a porous body or porous surfaces. Such materials can include ceramics, metals, and polymeric materials. In accordance with another embodiment, support member 20, mandrel 22, and/or lock member 24 can also be made to have a porous surface. Examples of suitable ceramics include, but are not limited to, zirconia, silica, glass, sintered calcium phosphates, calcium sulfate, and titanium dioxide.

Examples of suitable metals include, but are not limited to, 300 Series stainless steel, 400 Series stainless steel, titanium, tantalum, niobium, zirconium, hafnium, and cobalt chromium alloys. Surfaces having pores 44 can be made, for example, by sintering pre-formed metallic particles together to form porous blanks that can then be machined to a suitable shape or by sintering metallic particles together in a suitably-shaped mold. In alternative embodiments, the metal can be etched or bead-blasted to form a porous surface. Etching can be conducted by exposing the surface to a laser discharge, such as that of an excimer laser, or to a suitable chemical etchant.

Examples of suitable polymeric materials include, but are not limited to, regenerated cellulose, cellulose acetate, polyacetal, polyetheretherketone, polyesters, highly hydrolyzed polyvinyl alcohol, nylon, polyphenylenesulfide, polyethylene, polyethylene terephthalate, polypropylene, and combinations thereof. Methods of making polymers having pores 44, such as by foaming, sintering particles to form a porous block, and phase inversion processing, are understood by one of ordinary skill in the art. The polymeric material selected should not be capable of swelling, dissolving, or adversely reacting with the coating substance.

Figure 4A:
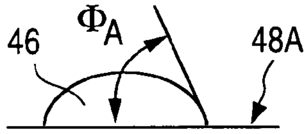
FIG. 4A illustrates a fluid on a solid substrate having a contact angle $\phi_A$.
Figure 4B:
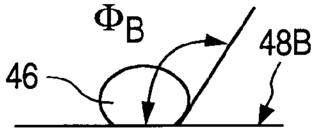
FIG. 4B illustrates a fluid on a solid substrate having a contact angle $\phi_B$.

In one suitable embodiment, the polymeric material from which the components are made is selected to allow the coating substance to have a high capillary permeation when a droplet of the coating substance is placed thereon. Capillary permeation or wetting is the movement of a fluid on a solid substrate driven by interfacial energetics. Capillary permeation is quantitated by a contact angle, defined as an angle at the tangent of a droplet in a fluid phase that has taken an equilibrium shape on a solid surface. A low contact angle indicates a higher wetting liquid. A suitably high capillary permeation corresponds to a contact angle less than about 90°. FIG. 4A illustrates a droplet 46 of the coating substance on a flat, nonporous surface 48A composed of the same material as coning end portion 30 or 36. Fluid droplet 46 has a high capillary permeation that corresponds to a contact angle $\phi_A$, which is less than about 90°. By contrast, FIG. 4B illustrates fluid droplet 46 on a surface 48B having a low capillary permeation that corresponds to a contact angle $\phi_B$, which is greater than about 90°. Surface treatments understood by one of ordinary skill in the art, such as plasma treating, corona treating, chemical oxidation, and etching, can be used to modify the surface to render the surface more capable of allowing the coating substance to have a suitably high capillary permeation.

Figure 5:
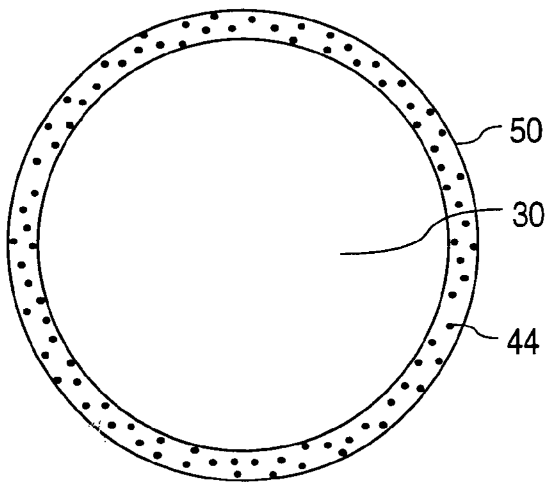
FIG. 5 illustrates an end view of a coning end portion having a porous covering over the outer surface thereof.

FIG. 5 illustrates an embodiment in which the outer surface of coning end portions 30 and/or 36 is covered with a layer 50. In such an embodiment, coning end portions 30 and/or 36 can have either porous or non-porous surfaces, while layer 50 can be made of an absorbent material, such as a sponge. Accordingly, layer 50 can absorb excess coating substance flowing off of stent 10. In addition, support member 20, mandrel 22, and/or lock member 24 can also be covered with layer 50.

While the device of the present invention has been described herein as having coning end portions 30 and 36 that support the respective ends of a stent and draw excess coating materials away from the stent via pores 44, it should be understood that the present invention is not limited thereto. Rather, the stent mounting assembly of the present invention can be any device that includes porous regions for supporting a stent as well as for absorbing excess coating materials to minimize coating defects.

Coating a Stent Using the Mounting Assembly

The following method of application is being provided by way of illustration and is not intended to limit the embodiments of mounting assembly 18 of the present invention. A spray apparatus, such as EFD 780S spray device with VALVEMATE 7040 control system (manufactured by EFD Inc., East Providence, R.I.), can be used to apply a composition to a stent. EFD 780S spray device is an air-assisted external mixing atomizer. The composition is atomized into small droplets by air and uniformly applied to the stent surfaces. The atomization pressure can be maintained at a range of about 5 psi to about 20 psi. The droplet size depends on such factors as viscosity of the solution, surface tension of the solvent, and atomization pressure. Other types of spray applicators, including air-assisted internal mixing atomizers and ultrasonic applicators, can also be used for the application of the composition.

During the application of the composition, a stent supported by mounting assembly 18 can be rotated about the stent's central longitudinal axis. Rotation of the stent can be from about 1 rpm to about 300 rpm, more narrowly from about 50 rpm to about 150 rpm. By way of example, the stent can rotate at about 120 rpm. The stent can also be moved in a linear direction along the same axis. The stent can be moved at about 1 mm/second to about 12 mm/second, for example about 6 mm/second, or for a minimum of at least two passes (i.e., back and forth past the spray nozzle). The flow rate of the solution from the spray nozzle can be from about 0.01 mg/second to about 1.0 mg/second, more narrowly about 0.1 mg/second. Multiple repetitions for applying the composition can be performed, wherein each repetition can be, for example, about 1 second to about 10 seconds in duration. The amount of coating applied by each repetition can be about 0.1 micrograms/$cm^2$ (of stent surface) to about 40 micrograms/$cm^2$, for example less than about 2 micrograms/$cm^2$ per 5-second spray.

Each repetition can be followed by removal of a significant amount of the solvent. Depending on the volatility of the particular solvent employed, the solvent can evaporate essentially upon contact with the stent. Alternatively, removal of the solvent can be induced by baking the stent in an oven at a mild temperature (e.g., 60° C.) for a suitable duration of time (e.g., 2-4 hours) or by the application of warm air. The application of warm air between each repetition prevents coating defects and minimizes interaction between the active agent and the solvent. The temperature of the warm air can be from about 30° C. to about 60° C., more narrowly from about 40° C to about 50° C. The flow rate of the warm air can be from about 20 cubic feet/minute (CFM) (0.57 cubic meters/minute (CMM)) to about 80 CFM (2.27 CMM), more narrowly about 30 CFM (0.85 CMM) to about 40 CFM (1.13 CMM). The warm air can be applied for about 3 seconds to about 60 seconds, more narrowly for about 10 seconds to about 20 seconds. By way of example, warm air applications can be performed at a temperature of about 50° C., at a flow rate of about 40 CFM, and for about 10 seconds. Any suitable number of repetitions of applying the composition followed by removing the solvent(s) can be performed to form a coating of a desired thickness or weight. Excessive application of the polymer in a single application can, however, cause coating defects.

Operations such as wiping, centrifugation, or other web clearing acts can also be performed to achieve a more uniform coating. Briefly, wiping refers to the physical removal of excess coating from the surface of the stent; and centrifugation refers to rapid rotation of the stent about an axis of rotation. The excess coating can also be vacuumed off of the surface of the stent.

In accordance with one embodiment, the stent can be at least partially pre-expanded prior to the application of the composition. For example, the stent can be radially expanded about 20% to about 60%, more narrowly about 27% to about 55%—the measurement being taken from the stent's inner diameter at an expanded position as compared to the inner diameter at the unexpanded position. The expansion of the stent, for increasing the interspace between the stent struts during the application of the composition, can further prevent "cob web" formation between the stent struts.

In accordance with one embodiment, the composition can include a solvent and a polymer dissolved in the solvent. The composition can also include active agents, radiopaque elements, or radioactive isotopes. Representative examples of polymers that can be used to coat a stent include ethylene vinyl alcohol copolymer (commonly known by the generic name EVOH or by the trade name EVAL); poly(hydroxyvalerate); poly(L-lactic acid); polycaprolactone; poly(lactide-co-glycolide); poly(hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly(trimethylene carbonate); poly(iminocarbonate); copoly(ether-esters) (e.g., PEO/PLA); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; and carboxymethyl cellulose.

"Solvent" is defined as a liquid substance or composition that is compatible with the polymer and is capable of dissolving the polymer at the concentration desired in the composition. Examples of solvents include, but are not limited to, dimethylsulfoxide (DMSO), chloroform, acetone, water (buffered saline), xylene, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, isopropanol admixed with water, N-methyl pyrrolidinone, toluene, and combinations thereof.

The active agent could be for inhibiting the activity of vascular smooth muscle cells. More specifically, the active agent can be aimed at inhibiting abnormal or inappropriate migration and/or proliferation of smooth muscle cells for the inhibition of restenosis. The active agent can also include any substance capable of exerting a therapeutic or prophylactic effect in the practice of the present invention. For example, the agent can be for enhancing wound healing in a vascular site or improving the structural and elastic properties of the vascular site. Examples of agents include antiproliferative substances such as actinomycin D, or derivatives and analogs thereof (manufactured by Sigma-Aldrich 1001 West Saint Paul Avenue, Milwaukee, WI 53233; or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, antiinflammatory, antiplatelet, anticoagulant, antifibrin, antithrombin, antimitotic, antibiotic, antiallergic and antioxidant substances. Examples of such antineoplastics and/or antimitotics include paclitaxel (e.g., TAXOL® by Bristol-Myers Squibb Co., Stamford, Conn.), docetaxel (e.g., Taxotere®, from Aventis S.A., Frankfurt, Germany), methotrexate, azathioprine, vincri stine, vinblastine, fluorouracil, doxorubicin hydrochloride (e.g., Adriamycin ® from Pharmacia & Upjohn, Peapack N.J.), and mitomycin (e.g., Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax ™ (Biogen, Inc., Cambridge, Mass.). Examples of such cytostatic or antiproliferative agents include angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil and Prinzide from Merck & Co., Inc., Whitehouse Station, NJ), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, NJ), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, rapamycin and dexamethasone. Exposure of the active ingredient to the composition should not adversely alter the active ingredient's composition or characteristic. Accordingly, the particular active ingredient is selected for compatibility with the solvent or blended polymer-solvent.

Examples of radiopaque elements include, but are not limited to, gold, tantalum, and platinum. An example of a radioactive isotope is $P^{32}$ Sufficient amounts of such substances may be dispersed in the composition such that the substances are not present in the composition as agglomerates or flocs.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of coating a stent, comprising:

positioning a stent on a mounting assembly, wherein a section of the mounting assembly includes a porous surface; and applying a coating composition to the stent, wherein the pores are configured to receive at least some of the coating composition applied to the stent that overflows from the stent during the application of the coating composition, wherein the mounting assembly includes a first member to make contact with a first end of the stent, and a second member to make contact with a second end of the stent, and wherein the pores are located on at least a region of a surface of the first or second member.

2. The method of claim 1, additionally comprising at least partially expanding the stent prior to applying the coating composition.

3. The method of claim 1, wherein the coating composition includes a solvent, a polymer dissolved in the solvent, and optionally a therapeutic substance.

4. The method of claim 1, additionally comprising rotating the stent about a longitudinal axis of the stent as the coating composition is applied to the stent.

5. The method of claim 1, additionally comprising moving the stent in a linear direction along a longitudinal axis of the stent as the coating composition is applied to the stent.

6. The method of claim 1, wherein applying the coating composition comprises spraying the coating composition onto the stent.

7. The method of claim 1, wherein the mounting assembly further includes a third member extending within the stent and securing the first member to the second member.

8. The method of claim 7, wherein the third member does not make contact with an inner surface of the stent.

9. A method of coating a stent, comprising:

positioning a stent on a mounting assembly, wherein a section of the mounting assembly includes a porous surface; and applying a coating composition to the stent, wherein the pores are configured to receive at least some of the coating composition applied to the stent that overflows from the stent during the application of the coating composition, wherein the pores have an open end and a closed end so as to provide a closed pore system on the surface of the mounting assembly.

10. The method of claim 1, wherein the pores are interconnected so as to provide an open pore system on the mounting assembly.

11. A method of coating a stent, comprising:

positioning a stent on a support member, wherein the support member includes an absorbing layer disposed on a surface of the support member; and applying a coating composition to the stent, wherein the absorbing layer is capable of at least partially absorbing some of the coating composition that comes into contact with the absorbing layer during the application of the coating composition, wherein the absorbing layer is in contact with an end of the stent during the application of the coating composition.

12. The method of claim 11, wherein the coating composition includes a solvent, a polymer dissolved in the solvent, and optionally a therapeutic substance.

13. The method of claim 11, additionally comprising rotating the stent about a longitudinal axis of the stent as the coating composition is applied to the stent.

14. The method of claim 11, additionally comprising moving the stent in a linear direction along a longitudinal axis of the stent as the coating composition is applied to the stent.

15. The method of claim 11, wherein applying the coating composition comprises spraying the coating composition onto the stent.

16. A method of coating a stent, comprising:

positioning a stent on a support member, wherein the support member includes an absorbent material; and applying a coating composition to the stent, wherein the support member is capable of at least partially absorbing some of the coating composition that comes into contact with the support member during the application of the coating composition, wherein the absorbing material is in contact with an end of the stent during the application of the coating composition.

17. The method of claim 16, wherein the coating composition includes a solvent, a polymer dissolved in the solvent, and optionally a therapeutic substance.

18. The method of claim 16, additionally comprising rotating the stent about a longitudinal axis of the stent as the coating composition is applied to the stent.

19. The method of claim 16, additionally comprising moving the stent in a linear direction along a longitudinal axis of the stent as the coating composition is applied to the stent.

20. The method of claim 16, wherein applying the coating composition comprises spraying the coating composition onto the stent.

21. A method of coating a stent, comprising:

positioning a first end of a stent to make contact with a first member of a mounting assembly;

positioning a second end of the stent to make contact with a second member of the mounting assembly; and applying a coating composition to the stent, wherein a section of the first or second member includes a porous surface capable of receiving some of the coating composition during the application of the coating composition.

22. The method of claim 21, wherein the first or second member is made from a metallic material.

23. The method of claim 22, wherein the metallic material is selected from the group consisting of stainless steel, titanium, tantalum, niobium, zirconium, hafnium, and cobalt chromium alloys.

24. The method of claim 21, wherein the first or second member is made from a polymeric material.

25. The method of claim 24, wherein the polymeric material is selected from the group consisting of regenerated cellulose, cellulose acetate, polyacetal, polyetheretherketone, polyesters, highly hydrolyzed polyvinyl alcohol, nylon, polyphenylenesulfide, polyethylene, polyethylene terephthalate, polypropylene, and combinations thereof.

26. The method of claim 21, wherein the first or second member is made from a ceramic material.

27. The method of claim 26, wherein the ceramic material is selected from the group consisting of zirconia, silica, glass, sintered calcium phosphates, calcium sulfate, and titanium dioxide.

28. The method of claim 21, wherein the first and second members have inwardly tapered ends that penetrate at least partially in the first and second ends of the stent.

29. The method of claim 21, wherein the mounting assembly additionally comprises a third member extending within the stent and securing the first member to the second member.

30. The method of claim 29, wherein an outer surface of the third member does not make contact with an inner surface of the stent.

31. The method of claim 21, wherein the coating composition includes a solvent, a polymer dissolved in the solvent, and optionally a therapeutic substance.

32. The method of claim 21, additionally comprising rotating the stent about a longitudinal axis of the stent as the coating composition is applied to the stent.

33. The method of claim 21, additionally comprising moving the stent in a linear direction along a longitudinal axis of the stent as the coating composition is applied to the stent.

34. The method of claim 21, wherein applying the coating composition comprises spraying the coating composition onto the stent.

35. A method of coating a stent, comprising:

positioning a first end of a stent so that the first end is supported by a first member of a mounting assembly;

positioning a second end of the stent so that the second end is supported by a second member of the mounting assembly; and applying a coating composition to the stent, wherein the first or second member includes cavities capable of receiving and containing at least some of the excess coating composition applied to the stent during the application of the coating composition.

36. The method of claim 35, wherein the mounting assembly additionally includes a third member extending within the stent and securing the first member to the second member, the method further comprising adjusting the distance between the first member and the second member by inserting the third member deeper into the first member or the second member.

37. The method of claim 35, wherein the coating composition includes a solvent, a polymer dissolved in the solvent, and optionally a therapeutic substance.

38. The method of claim 35, additionally comprising rotating the stent about a longitudinal axis of the stent as the coating composition is applied to the stent.

39. The method of claim 35, additionally comprising moving the stent in a linear direction along a longitudinal axis of the stent as the coating composition is applied to the stent.

40. The method of claim 35, wherein applying the coating composition comprises spraying the coating composition onto the stent.

41. A method of coating a stent, comprising:

positioning a first end of a stent so that the first end is supported by a first member of a mounting assembly;

positioning a second end of the stent so that the second end is supported by a second member of the mounting assembly; and applying a coating composition to the stent, wherein the first or second member includes a layer disposed on a surface of the first or second member, wherein the layer absorbs at least some of the coating composition that comes into contact with the layer during the application of the coating composition.

42. The method of claim 41, wherein the coating composition includes a solvent, a polymer dissolved in the solvent, and optionally a therapeutic substance 43. The method of claim 41, additionally comprising rotating the stent about a longitudinal axis of the stent as the coating composition is applied to the stent.

44. The method of claim 41, additionally comprising moving the stent in a linear direction along a longitudinal axis of the stent as the coating composition is applied to the stent.

45. The method of claim 41, wherein applying the coating composition comprises spraying the coating composition onto the stent.

46. A method of coating a stent, comprising:

positioning a stent on a mounting assembly, the mounting assembly comprising a first member to support a first end of a stent, a second member to support a second of the stent, and a third member extending through the stent and connecting the first member to the second member;

applying a coating composition to the stent, wherein a surface of the third member includes pores that receives a portion of the coating composition that comes in contact with the surface of the third member during the application of the coating composition; and rotating the stent about a longitudinal axis of the stent as the coating composition is applied to the stent.

47. The method of claim 46, wherein the third member does not contact an inner surface of the stent.

48. The method of claim 46, wherein the coating composition includes a solvent, a polymer dissolved in the solvent, and optionally a therapeutic substance.

49. A method of coating a stent, comprising:

positioning a stent on a mounting assembly, the mounting assembly comprising a first member to support a first end of a stent, a second member to support a second of the stent, and a third member extending through the stent and connecting the first member to the second member;

applying a coating composition to the stent, wherein a surface of the third member includes pores that receives a portion of the coating composition that comes in contact with the surface of the third member during the application of the coating composition; and moving the stent in a linear direction along a longitudinal axis of the stent as the coating composition is applied to the stent.

50. A method of coating a stent, comprising:

positioning a stent on a mounting assembly, the mounting assembly comprising a first member to support a first end of a stent, a second member to support a second of the stent, and a third member extending through the stent and connecting the first member to the second member; and applying a coating composition to the stent, wherein a surface of the third member includes pores that receives a portion of the coating composition that comes in contact with the surface of the third member during the application of the coating composition; and wherein applying the coating composition comprises spraying the coating composition onto the stent.

51. A method of coating a stent, comprising:

positioning a stent on a mounting assembly including the step of pinching the stent between a first member and a second member of the mounting assembly, the mounting assembly further including a third member extending through the stent and connecting the first member to the second member; and applying a coating composition to the stent, wherein the third member includes an absorbing layer or is made from an absorbent material that at least partially absorbs some of the coating composition that comes in contact with the third member during the application of the coating composition.

52. The method of claim 51, wherein the third member does not contact an inner surface of the stent.

53. The method of claim 51, wherein the coating composition includes a solvent, a polymer dissolved in the solvent, and optionally a therapeutic substance.

54. The method of claim 51, additionally comprising rotating the stent about a longitudinal axis of the stent as the coating composition is applied to the stent.

55. The method of claim 51, additionally comprising moving the stent in a linear direction along a longitudinal axis of the stent as the coating composition is applied to the stent.

56. The method of claim 51, wherein applying the coating composition comprises spraying the coating composition onto the stent.

57. A method of coating a stent, comprising:

positioning a stent on a support member, the member including a first member for making contact with a first end of the stent and a second member for making contact with a second end of the stent; and applying a coating composition to the stent, wherein the first or second member is made from an absorbent material capable of at least partially absorbing at least some of the coating composition that comes into contact with the first or second member during the application of the coating composition.

58. The method of claim 57, wherein the coating composition includes a solvent, a polymer dissolved in the solvent, and optionally a therapeutic substance.

59. The method of claim 57, additionally comprising rotating the stent about a longitudinal axis of the stent as the coating composition is applied to the stent.

60. The method of claim 57, additionally comprising moving the stent in a linear direction along a longitudinal axis of the stent as the coating composition is applied to the stent.

61. The method of claim 57, wherein applying the coating composition comprises spraying the coating composition onto the stent.

62. The method of claim 49 wherein the third member does not contact an inner surface of the stent.

63. The method of claim 49 wherein the coating composition includes a solvent, a polymer dissolved in the solvent, and optionally a therapeutic substance.

64. The method of claim 50. wherein the third member does not contact an inner surface of the stent.

65. The method of claim 50 wherein the coating composition includes a solvent, a polymer dissolved in the solvent, and optionally a therapeutic substance.

* * * * *